(12) United States Patent
Kim

(10) Patent No.: US 12,023,872 B1
(45) Date of Patent: Jul. 2, 2024

(54) PERSONALIZED INSOLE PRODUCTION SYSTEM AND METHODS

(71) Applicant: Namhee Kim, Goyang-si (KR)

(72) Inventor: Namhee Kim, Goyang-si (KR)

( * ) Notice: Subject to any disclaimer, the term of this patent is extended or adjusted under 35 U.S.C. 154(b) by 0 days.

(21) Appl. No.: 18/426,400

(22) Filed: Jan. 30, 2024

Related U.S. Application Data

(60) Provisional application No. 63/597,331, filed on Nov. 8, 2023, provisional application No. 63/597,333, filed on Nov. 8, 2023.

(51) Int. Cl.
*B29C 64/393* (2017.01)
*A61B 5/00* (2006.01)
*A61B 5/103* (2006.01)
*B29D 35/12* (2010.01)
*B33Y 50/02* (2015.01)
*B33Y 80/00* (2015.01)

(52) U.S. Cl.
CPC .......... *B29C 64/393* (2017.08); *A61B 5/1036* (2013.01); *A61B 5/702* (2013.01); *B29D 35/122* (2013.01); *B33Y 50/02* (2014.12); *B33Y 80/00* (2014.12); *A61B 2503/12* (2013.01)

(58) Field of Classification Search
CPC ..... B29C 64/393; A61B 5/1036; A61B 5/702; A61B 2503/12; B29D 35/122; B33Y 50/02; B33Y 80/00
See application file for complete search history.

(56) References Cited

U.S. PATENT DOCUMENTS

| | | | | |
|---|---|---|---|---|
| 5,101,580 | A * | 4/1992 | Lyden | A43B 7/20 36/43 |
| 7,069,665 | B1 * | 7/2006 | Adriano | A43B 7/24 36/43 |
| 9,460,557 | B1 * | 10/2016 | Tran | G06T 15/205 |
| 9,721,384 | B1 * | 8/2017 | Tran | A43B 17/14 |
| 9,820,530 | B2 * | 11/2017 | Cross | A43B 13/22 |
| 9,836,883 | B2 * | 12/2017 | Tran | A43B 3/34 |
| 10,182,615 | B2 * | 1/2019 | Jacobsen | B32B 5/18 |
| 10,279,581 | B2 * | 5/2019 | Ashcroft | A43B 13/223 |
| 10,293,565 | B1 * | 5/2019 | Tran | A43D 1/02 |

(Continued)

FOREIGN PATENT DOCUMENTS

| | | |
|---|---|---|
| KR | 10-2015372 B1 | 8/2019 |
| KR | 10-2023-0083717 A | 6/2023 |
| KR | 10-2023-0083748 A | 6/2023 |

*Primary Examiner* — Ramesh B Patel
(74) *Attorney, Agent, or Firm* — You & IP, LLC

(57) ABSTRACT

Personalized insole manufacturing apparatus and method includes a foot pressure pattern measuring unit configured to measure user's foot pressure pattern, a foot pressure pattern image acquisition unit configured to capture an image of the foot pressure pattern printed on the foot pressure pattern measuring unit and combine the captured image with a foot shape image, a foot pressure pattern pressure calculation unit configured to divide the combined image into a predetermined number of areas, and calculate a pressure level for each area, an insole attachment calculation unit configured to calculate data of an attachment pad corresponding to the foot pressure pattern, and an insole attachment output unit configured to visually show the attachment pad or data calculated by the insole attachment calculation unit.

18 Claims, 7 Drawing Sheets

(56) References Cited

U.S. PATENT DOCUMENTS

| | | | | |
|---|---|---|---|---|
| 10,299,722 | B1* | 5/2019 | Tran | B33Y 80/00 |
| 10,482,214 | B2* | 11/2019 | Cluckers | B33Y 80/00 |
| 10,681,961 | B2* | 6/2020 | Jarvis | A43B 9/02 |
| 10,891,785 | B2* | 1/2021 | Tran | G06T 17/00 |
| 11,432,617 | B2* | 9/2022 | Kohatsu | A61B 5/1036 |
| 11,612,209 | B2* | 3/2023 | Ashcroft | A43B 5/06 |
| | | | | 702/138 |
| 11,647,805 | B2* | 5/2023 | Busbee | B29C 64/209 |
| | | | | 73/172 |
| 2004/0194344 | A1* | 10/2004 | Tadin | A43B 7/145 |
| | | | | 36/173 |
| 2007/0043582 | A1* | 2/2007 | Peveto | A43B 23/027 |
| | | | | 705/26.1 |
| 2017/0027277 | A1* | 2/2017 | Anthony | A43B 7/28 |
| 2017/0272728 | A1* | 9/2017 | Rafii | G06Q 30/0631 |
| 2019/0297995 | A1* | 10/2019 | Loveder | A43B 7/148 |
| 2023/0339200 | A1* | 10/2023 | Shih | B29D 35/061 |

* cited by examiner

PERSONALIZED INSOLE PRODUCTION SYSTEM AND METHODS

CROSS-REFERENCE TO RELATED APPLICATION

This application claims priority under 35 U.S.C § 119 to U.S. Provisional Application Ser. No. 63/597,331 filed Nov. 8, 2023, and Ser. No. 63/597,333 filed Nov. 8, 2023, respectively, the entire contents of which are hereby incorporated by reference.

TECHNICAL FIELD

The present disclosure relates to personalized insole production system and methods, and more specifically, to personalized insole production system and methods capable of manufacturing personalized insoles that fit the physical characteristics of each user more conveniently and quickly at a much lower cost.

BACKGROUND

Since the time humans began walking upright, the form of human gait has been used as measurement data to indirectly evaluate health, and accordingly, various methodologies to analyze the form of gait have been studied.

The related podoscope used as a foot pressure analysis device is capable of determining pressure distribution. It is configured so that, when the foot is placed on a transparent glass with a light attached to one side, the center of gravity and pressure of the foot can be seen through a mirror attached to the floor. The brightly visible part of the sole indicates high pressure, and the condition of the foot, such as normal foot, cavus foot, flat foot, linear foot, equinus foot, hallux valgus foot, etc. can be determined from the pressure of the sole reflected in the mirror on the floor.

In recent years, various foot pressure analysis apparatus using a pressure sensor unit that measures the pressure on the sole of the foot have been proposed, and while these apparatus can advantageously provide accurate and precise foot pressure measurements with various sensors attached thereto, there are disadvantages that the foot pressure measuring apparatus itself is quite expensive, making it difficult for general users to purchase without burden, and that it is also not able to analyze foot pressure in actual moving conditions.

Accordingly, Korean Registered Patent No. 10-2015372 (entitled "Apparatus for measuring foot pressure patterns and insole combination guiding method using same"), which was filed by the same inventor of the present disclosure and registered as a patent, proposes a foot pressure pattern measuring apparatus includes a first color layer attached with a first color material, a second color layer attached with a second color material, a print layer, and a protective layer, and after cutting along the cutting guide line marked on the upper surface of the first color layer, the user inserts it into the user's shoe such that the protective layer is positioned on the bottom, and after inserting, the user wears the shoes and makes predetermined steps, thus applying compression and pressure according to the shape of the sole of the foot, and foot pressure can be measured through the color that appears as the material of each color layer moves to the print layer according to the size of the applied compression and pressure.

However, in the related art, there are problems. That is, the large number of attachments required to be attached to the insole through the measured foot pressure pattern and positions and types thereof increase the manufacturing cost, and it is difficult for the user to attach multiple attachments to the insole. Further, it is difficult to manufacture an accurate and personalized insole, because the attachments to be attached to the insole are calculated by taking into account only the pressure force applied by the body weight distribution and movement during the user's gait, and the degree of distortion or rotation of the user's pelvis, which greatly affects the user's floor pressure during gait, or the existing medical conditions that each user may have are not taken into account.

SUMMARY

In order to solve one or more problems (e.g., the problems described above and/or other problems not explicitly described herein), the present disclosure is provided to enable a user to more conveniently manufacture a personalized insole by simplifying the positions and types of attachments required to be attached to the insole through measured foot pressure pattern.

In addition, the present disclosure is provided to enable the user to manufacture a more accurate and personalized insole in response to the individual user's physical characteristics or medical conditions, by calculating the positions and types of the insole attachment after considering not only the pressure applied by the body weight distribution and movement that appears during the user's gait, but also the degree of distortion of the user's pelvis and the existing medical conditions that each user may have.

To solve the problems described above, an embodiment of the personalized insole manufacturing apparatus according to the claimed invention comprises a foot pressure pattern measuring unit configured to measure user's foot pressure pattern, wherein the foot pressure pattern measuring unit has adhesive properties so as to be attached to a sole of the user's foot and is configured to print differently between an area on which a high pressure is applied by the user's body weight and an area on which a low pressure is applied; a foot pressure pattern image acquisition unit configured to capture an image of the foot pressure pattern printed on the foot pressure pattern measuring unit and combine the captured image with a foot shape image, wherein the foot pressure pattern image acquisition unit includes a camera and an image processing application; a user input unit including a keyboard, mouse, or microphone, wherein the user input unit is configured to receive information from a user; a foot pressure pattern pressure calculation unit including a processor configured to receive, from the foot pressure pattern image acquisition unit, a combined image of the foot pressure pattern and the foot shape image, divide the received combined image into a predetermined number of areas according to a predetermined criteria, analyze the foot pressure pattern printed in each area, and calculate a pressure level for each area; an insole attachment calculation unit including a processor configured to calculate data on shape, height, strength, elasticity, or material of an attachment pad corresponding to the foot pressure pattern based on the pressure level for each area received from the foot pressure pattern pressure calculation unit; and an insole attachment output unit including a display configured to visually show the attachment pad or data calculated by the insole attachment calculation unit, or a speaker configured to provide voice guidance, wherein the foot pressure pattern measuring unit includes a thin plate-shaped pad that displays the area on which the large pressure is applied by the body weight and the area on which the small pressure is applied with different ink densities or different colors, and the processors included in the foot pressure pattern pressure calculation unit and the insole attachment calculation unit are hardware processors or software processors, and the processors included in the foot pressure pattern pressure calculation unit and the insole attachment calculation unit are separate processors or the same processor.

Another embodiment of the personalized insole manufacturing apparatus according to the claimed invention further comprises an insole attachment unit provided with a plurality of attachment pads having different combinations of shapes, heights, strengths, and materials, wherein the insole attachment calculation unit displays the calculated attachment pads through a display.

In another embodiment of the personalized insole manufacturing apparatus according to the claimed invention, the foot pressure pattern pressure calculation unit divides the predetermined number of areas on the combined image into: a toe area corresponding to a toe portion; a forefoot area corresponding to an area from below the toe area to where arch begins; a midfoot area corresponding to an area from where the arch ends to where heel begins; and a rearfoot area corresponding to a heel area.

In another embodiment of the personalized insole manufacturing apparatus according to the claimed invention, the foot pressure pattern pressure calculation unit further divides the predetermined number of areas on the combined foot pressure pattern image into: for the toe area, a first area as an area including a first toe, and a second area as an area including four other toes except the first toe; for the forefoot area, a third area as an inner area of the forefoot area, a fourth area as a middle area, and a fifth area as an outer area, for the midfoot area, a sixth area as an inner area with respect to a center and a seventh area as an outer area with respect to the center, and for the rearfoot area, an eighth area as an inner area with respect to the center and a ninth area as an outer area with respect to the center, and calculates a pressure level of each area based on the foot pressure pattern shown in each area.

In another embodiment of the personalized insole manufacturing apparatus according to the claimed invention, the attachment pad calculated by the insole attachment calculation unit includes: a meta-dome pad configured to support a sole of the user's foot at a position corresponding to a lower central area of the third to fifth areas and an upper central area of the sixth and seventh areas of the combined image; an arch pad configured to support the sole of a user's foot at a position corresponding to an inside of the sixth area of the combined image; a forefoot lateral wedge pad configured to support the sole of the user's foot at a position corresponding to an outside of the seventh area of the combined image; a medial heel wedge pad configured to support the sole of the user's foot at a position corresponding to an inside of the eighth area of the combined image; and a lateral heel wedge pad configured to support the sole of the user's foot at a position corresponding to an outside of the ninth area of the combined image, and the insole attachment calculation unit calculates each pad by varying a combination of shape, height, strength, and material.

In another embodiment of the personalized insole manufacturing apparatus according to the claimed invention, the insole attachment output unit is a 3D printer or molding apparatus configured to receive the data about the attachment pad calculated by the insole attachment calculation unit and manufacture the attachment pad.

In another embodiment of the personalized insole manufacturing apparatus according to the claimed invention, the insole attachment calculation unit is configured to: compare a virtual boundary line of the sixth and seventh areas with a virtual central reference line connecting a front central point of the second toe and a rear central point of a rearfoot of the foot pressure pattern in a straight line, and when the center line and the central reference line coincide with each other within a predetermined error range, calculate the meta-dome pad, the arch pad, and the forefoot lateral wedge pad to have a first level thickness; when the center line does not coincide with the central reference line within the predetermined error range and the boundary line of the foot pressure pattern of the midfoot is in the sixth area, calculate the meta-dome pad and the forefoot lateral wedge pad to have the first level thickness, and calculate the arch pad to have a second level thickness which is higher than the first level; and when the center line does not coincide with the central reference line within the predetermined error range and the boundary line of the foot pressure pattern of the midfoot is in the seventh area, calculate the meta-dome pad and arch pad to have the first level thickness, and calculate the forefoot lateral wedge pad to have the second level thickness which is higher than the first level.

In another embodiment of the personalized insole manufacturing apparatus according to the claimed invention, the insole attachment calculation unit is configured to: when the pressure level of the eighth area is higher than the pressure level of the ninth area, calculate the medial heel wedge pad to have a predetermined height; and when the pressure level of the eighth area is lower than the pressure level of the ninth area, calculate the lateral heel wedge pad to have a predetermined height.

In another embodiment of the personalized insole manufacturing apparatus according to the claimed invention, the insole attachment calculation unit is configured to: when the pressure level of the third area and the pressure level of the fourth area are greater than the pressure level of the fifth area, recalculate each thickness of the arch pad and the meta-dome pad by increasing the thickness by one level; and when the pressure level of the fifth area is greater than the pressure levels of the third and fourth areas, recalculate the thickness of the forefoot lateral wedge pad by increasing the thickness by one level.

In another embodiment of the personalized insole manufacturing apparatus according to the claimed invention, the insole attachment calculation unit is configured to: after the user looks straight ahead, walks in place and then stops, if information is received from the input unit that a user's left foot is positioned ahead of the right foot, recalculate the thickness of the forefoot lateral wedge pad of the right foot by increasing the thickness by one level; and when information is received from the input unit that the right foot is positioned ahead of the left foot relative to the reference line, recalculate the thicknesses of the arch pad and the meta-dome pad of the right foot by increasing each thickness by one level.

Another embodiment of the personalized insole manufacturing apparatus according to the claimed invention further comprises a container provided with the meta-dome pad, the arch pad, the forefoot lateral wedge pad, the medial heel wedge pad, and the lateral heel wedge pad manufactured in advance, wherein the pads have first to third levels of thicknesses.

An embodiment of a method for manufacturing a personalized insole according to the claimed invention comprises: attaching a foot pressure pattern measurement pad to a sole of a user's foot to measure a user's foot pressure pattern when a user walks a predetermined distance; capturing, by a camera, an image of the foot pressure pattern printed on the foot pressure pattern measurement pad, and generating, by an image processing application, a combined image by combining the foot pressure pattern with a foot shape image; by a foot pressure pattern pressure calculation processor, dividing the combined image into a predetermined number of areas according to a predetermined criteria, analyzing the foot pressure pattern printed in each area, and calculating a pressure level for each area; calculating, by an insole attachment calculation processor, data on shape, height, strength, elasticity, or material of an attachment pad corresponding to the foot pressure pattern based on the pressure level of each area received from the foot pressure pattern pressure calculation processor; and outputting, through one or more of a display, a speaker, a 3D printer, or a molding apparatus, the attachment pad or the data calculated by the insole attachment calculation processor, wherein the foot pressure pattern displays an area on which a large pressure is applied by body weight and an area on which a small pressure is applied with different ink densities or different colors, and the predetermined number of areas on the combined foot pressure pattern image divided by the foot pressure pattern pressure calculation processor are divided into: a toe area corresponding to a toe portion; a forefoot area corresponding to an area from below the toe area to where arch begins; a midfoot area corresponding to an area from where the arch ends to where heel begins; and a rearfoot area corresponding to a heel area.

In another embodiment of the method according to the claimed invention, comprising further dividing the predetermined number of areas on the combined foot pressure pattern image into: for the toe area, a first area as an area including a first toe, and a second area as an area including four other toes except the first toe; for the forefoot area, a third area as an inner area of the forefoot area, a fourth area as a middle area, and a fifth area as an outer area; for the midfoot area; a sixth area as an inner area with respect to a center and a seventh area as an outer area with respect to the center; and for the rearfoot area, an eighth area as an inner area with respect to the center and a ninth area as an outer area with respect to the center, and calculating a pressure level of each area based on the foot pressure pattern shown in each area.

In another embodiment of the method according to the claimed invention, the attachment pad calculated by the insole attachment calculation processor includes: a meta-dome pad configured to support a sole of the user's foot at a position corresponding to a lower central area of the third to fifth areas and an upper central area of the sixth and seventh areas of the combined image; an arch pad configured to support the sole of a user's foot at a position corresponding to an inside of the sixth area of the combined image; a forefoot lateral wedge pad configured to support the sole of the user's foot at a position corresponding to an outside of the seventh area of the combined image; a medial heel wedge pad configured to support the sole of the user's foot at a position corresponding to an inside of the eighth area of the combined image; and a lateral heel wedge pad configured to support the sole of the user's foot at a position corresponding to an outside of the ninth area of the combined image, and the insole attachment calculation processor calculates each pad by varying a combination of shape, height, strength, and material.

In another embodiment of the method according to the claimed invention, the calculating, by the insole attachment calculation processor, the data on the shape, height, strength, elasticity, or material of the attachment pad includes: comparing a virtual boundary line of the sixth and seventh areas with a virtual central reference line connecting a front central point of the second toe and a rear central point of a rearfoot of the foot pressure pattern in a straight line, and when the center line and the central reference line coincide with each other within a predetermined error range, calculating the meta-dome pad, the arch pad, and the forefoot lateral wedge pad to have a first level thickness; when the center line does not coincide with the central reference line within the predetermined error range and the boundary line of the foot pressure pattern of the midfoot is in the sixth area, calculating the meta-dome pad and the forefoot lateral wedge pad to have the first level thickness, and calculating the arch pad to have a second level thickness which is higher than the first level; and when the center line does not coincide with the central reference line within the predetermined error range and the boundary line of the foot pressure pattern of the midfoot is in the seventh area, calculating the meta-dome pad and arch pad to have the first level thickness, and calculating the forefoot lateral wedge pad to have the second level thickness which is higher than the first level.

In another embodiment of the method according to the claimed invention, the calculating, by the insole attachment calculation processor, the data on the shape, height, strength, elasticity, or material of the attachment pad includes: when the pressure level of the eighth area is higher than the pressure level of the ninth area, calculating the medial heel wedge pad; and when the pressure level of the eighth area is lower than the pressure level of the ninth area, calculating the lateral heel wedge pad.

In another embodiment of the method according to the claimed invention, the calculating, by the insole attachment calculation processor, the data on the shape, height, strength, elasticity, or material of the attachment pad includes: when the pressure level of the third area and the pressure level of the fourth area are greater than the pressure level of the fifth area, respectively, recalculating each thickness of the arch pad and the meta-dome pad by increasing the thickness by one level; and when the pressure level of the fifth area is greater than the pressure levels of the third and fourth areas, respectively, recalculating the thickness of the forefoot lateral wedge pad by increasing the thickness by one level.

In another embodiment of the method according to the claimed invention, the calculating, by the insole attachment calculation processor, the data on the shape, height, strength, elasticity, or material of the attachment pad includes: after the user looks straight ahead, walks in place and then stops, if information is received from the input unit that a user's left foot is positioned ahead of the right foot, recalculating the thickness of the forefoot lateral wedge pad of the right foot by increasing the thickness by one level; and when information is received from the input unit that the right foot is positioned ahead of the left foot relative to the reference line, recalculating the thicknesses of the arch pad and the meta-dome pad of the right foot by increasing each thickness by one level.

The apparatus and method for manufacturing a personalized insole according to the embodiments of the present disclosure enable a user to more conveniently manufacture a personalized insole by simplifying the positions and types of attachments required to be attached to the insole through the measured foot pressure pattern.

In addition, the apparatus and method for manufacturing a personalized insole according to the embodiments of the present disclosure enable the user to manufacture a more accurate and personalized insole in response to the individual user's physical characteristics or medical conditions, by calculating the positions and types of the insole attachment after considering not only the pressure applied by the body weight distribution and movement that appears during the user's gait, but also the degree of distortion of the user's pelvis and the existing medical conditions that each user may have.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Hereinafter, example details for the realization of the objects of the present disclosure described above will be described with reference to the attached drawings. In describing the embodiments, the same names and symbols are used for the same components, and redundant description thereof will be omitted below.

Figure 1:
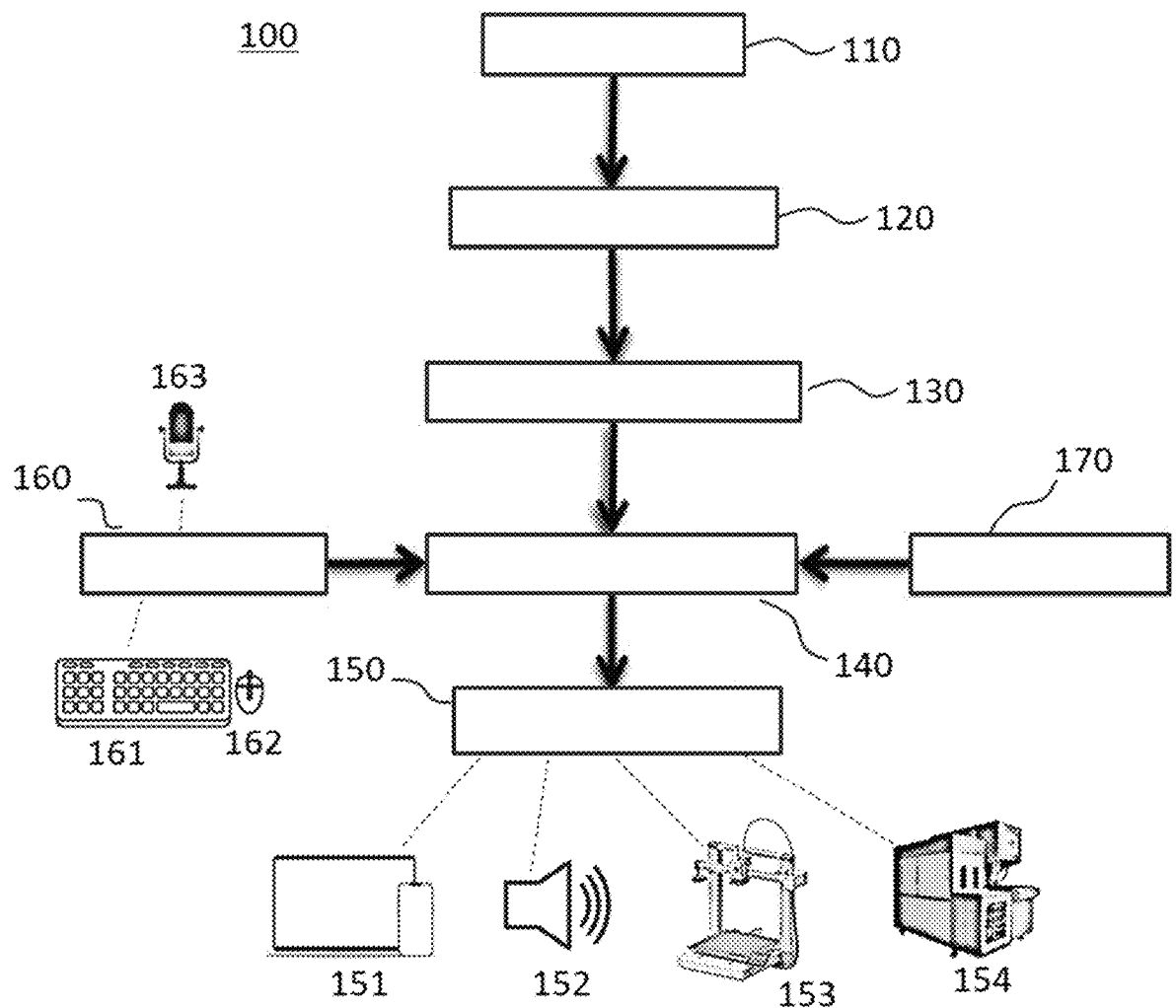
FIG. 1 is an apparatus configuration diagram showing a personalized insole manufacturing apparatus according to an embodiment.

FIG. 1 is an apparatus configuration diagram showing a personalized insole manufacturing apparatus according to an embodiment.

As shown in FIG. 1, a personalized insole manufacturing apparatus 100 according to an embodiment includes a foot pressure pattern measuring unit 110 that is configured to be attached to the sole of the user's foot and that prints the user's foot pressure pattern that appears when the user walks a predetermined distance, a foot pressure pattern image acquisition unit 120 that captures an image of the user's foot pressure pattern printed on the foot pressure pattern measuring unit 110 and combines the capture image with a foot shape image, a foot pressure pattern pressure calculation unit 130 that receives the combined image of the foot pressure pattern and the foot shape image from the foot pressure pattern image acquisition unit 120, divides the received combined image into a predetermined number of areas according to a predetermined criteria, and calculates a pressure level for each area, an insole attachment calculation unit 140 that calculates design-related data such as shape, height, strength, and material of a pad to be attached to the user's insole based on the pressure level for each area input from the foot pressure pattern pressure calculation unit, and an insole attachment output unit 150 that outputs data related to the attachment pad suitable for the user which is calculated by the insole attachment calculation unit 140. Hereinafter, the expression "shape, height, strength and material" refers to each of the shape, the height, the strength or the material, or a combination including at least one or more of these.

In addition, the personalized insole manufacturing apparatus 100 may further include a user input unit 160 configured to receive necessary information from the user, and an insole attachment unit 170 provided with attachment pads having various shapes, heights, strengths, and materials.

Figure 2:
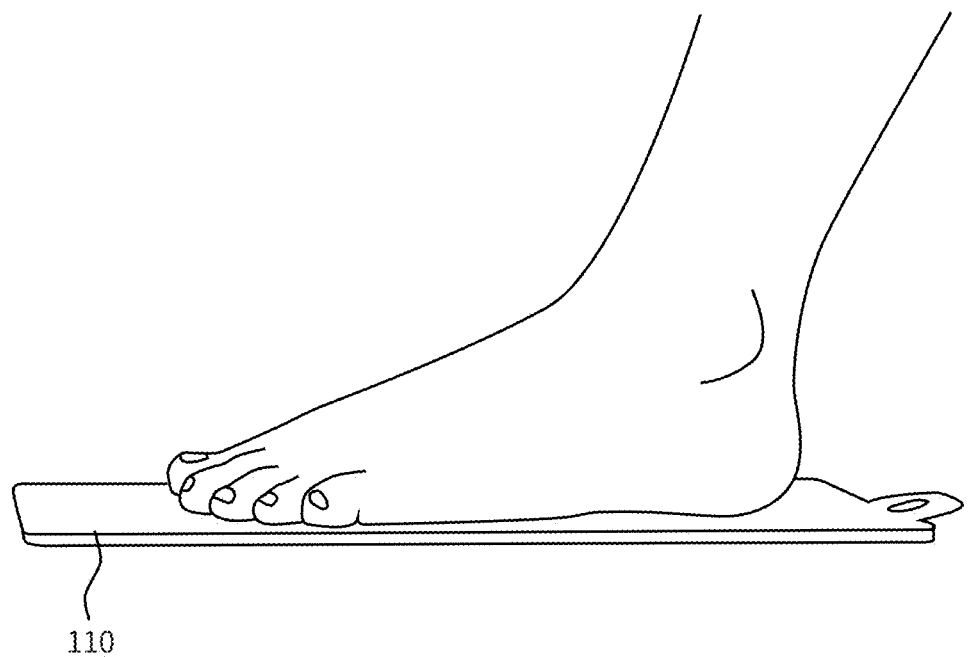
FIG. 2 is a diagram showing a foot pressure pattern measuring unit in use state.
Figure 3:
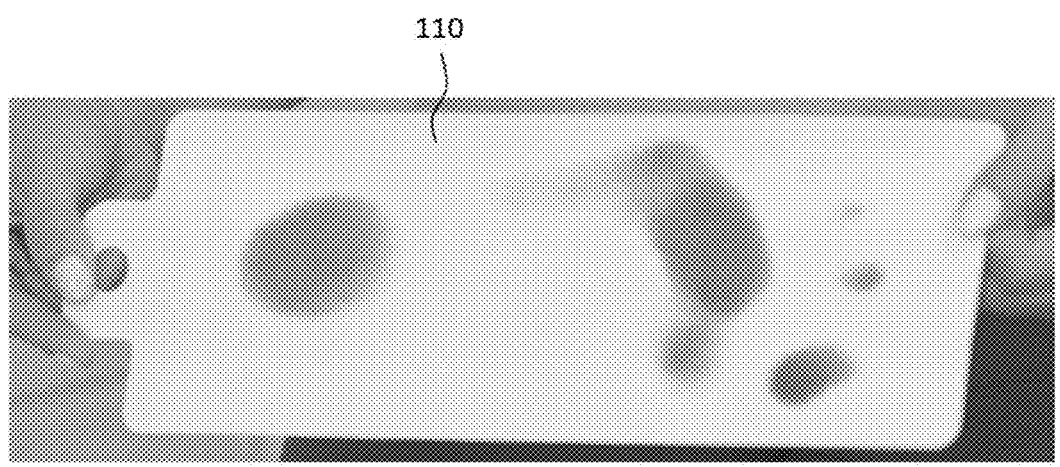
FIG. 3 is a diagram showing user's foot pressure pattern printed on the foot pressure pattern measuring unit.

The foot pressure pattern measuring unit 110 is an apparatus that can print a foot pressure pattern reflecting changes occurring in the body weight pressure according to the user's gait as the user walks a predetermined distance with his foot placed on the foot pressure pattern measuring unit 110. At this time, the foot pressure pattern may appear as the difference in ink density or color. The structure of the foot pressure pattern measuring unit 110 may be any structure as long as it can indicate changes in the body weight pressure. For example, as shown in FIGS. 2 and 3, the foot pressure pattern measuring unit 110 may be a thin plate-shaped pad that has adhesive properties so as to be attached to the sole of the user's foot, and that shows a higher ink density in an area where the higher pressure is applied by the body weight and shows a lower ink density in an area where the lower pressure is applied. Alternatively, the foot pressure pattern measuring unit 110 may be a thin plate-shaped pad that shows different colors in the area where the higher pressure is applied by the body weight and in the area where the lower pressure is applied. The foot pressure pattern measuring unit 110 may be provided as a pair that may include left and right units, or, if necessary, may be provided as one unit that may be either the left unit or the right unit. However, for convenience of explanation, an example having both the left and right units will be described below.

The foot pressure pattern image acquisition unit 120 may capture a still image of the user's foot pressure pattern printed on the foot pressure pattern measuring unit 110, and may acquire only the images of specific areas, that is, the images of the left and right foot pressure patterns from the entire still images. In addition, the foot pressure pattern image acquisition unit 120 may generate a combined image 200 by combining the acquired foot pressure pattern image with an image of the user's foot shape or a foot shape similar to the user's body shape. The foot pressure pattern image acquisition unit 120 may be a built-in camera 122 or an image sensor usually built into a mobile device such as a smartphone or a tablet PC. In addition, the foot pressure pattern image acquisition unit 120 may be provided with an image processing application, and the image processing application may acquire the left, right, or left and right foot pressure pattern from the captured image and combine the acquired pressure patterns with the images of each foot shape. Hereinafter, the image combining the foot pressure pattern and the foot shape image may also be referred to as "combined foot pressure pattern image" 200. When using the camera 122 built into the mobile device as the image acquisition unit 120, a dedicated application may be installed on the mobile device to facilitate acquisition of the foot pressure pattern images. Combining the foot pressure pattern and the foot shape image does not necessarily need to be performed in the foot pressure pattern image acquisition unit 120. If necessary, the foot pressure pattern image acquisition unit 120 may only acquire the foot pressure pattern and transmit the acquired pattern to the foot pressure pattern pressure calculation unit 130, which will be described below, and the foot pressure pattern pressure calculation unit 130 may combine the images.

Figure 5:
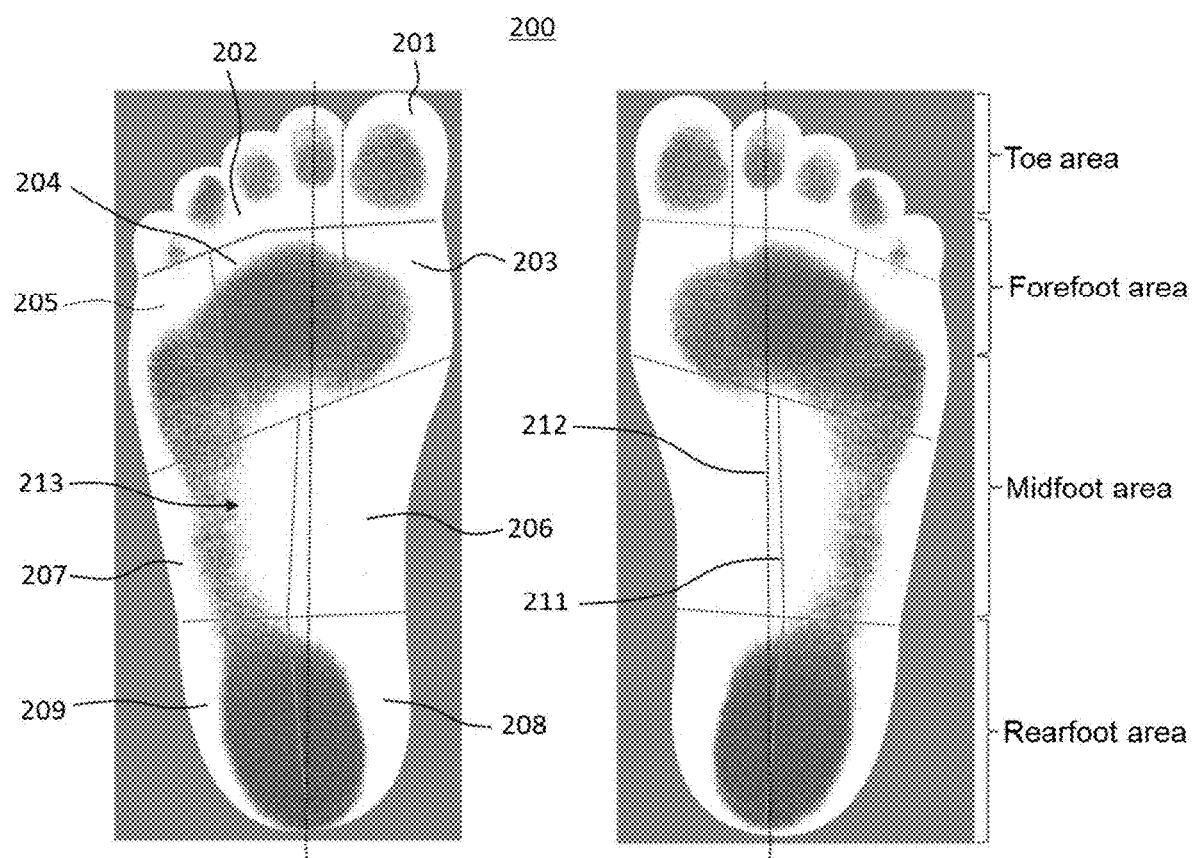
FIG. 5 is a foot pressure pattern area division diagram showing the foot pressure pattern divided into a total of 9 areas including first to ninth areas, in a personalized insole manufacturing apparatus according to an embodiment.

As shown in FIG. 5, the foot pressure pattern pressure calculation unit 130 receives the image combining the foot pressure pattern acquired at the foot pressure pattern image acquisition unit 120 and the foot shape, and divides the received image into a predetermined number of areas. The combined foot pressure pattern image may be an image of the left or right side, or only the left and right sides, or both sides. When the combined foot pressure pattern image 200 is not created by the foot pressure pattern image acquisition unit 120, the pressure calculation unit 130 may create a combined foot pressure pattern image by combining the foot pressure pattern transmitted from the foot pressure pattern image acquisition unit 120 and the foot shape image. Meanwhile, the foot pressure pattern pressure calculation unit 130 may be a software application installed in the device, or may be a dedicated or general-purpose hardware processor.

Figure 6:
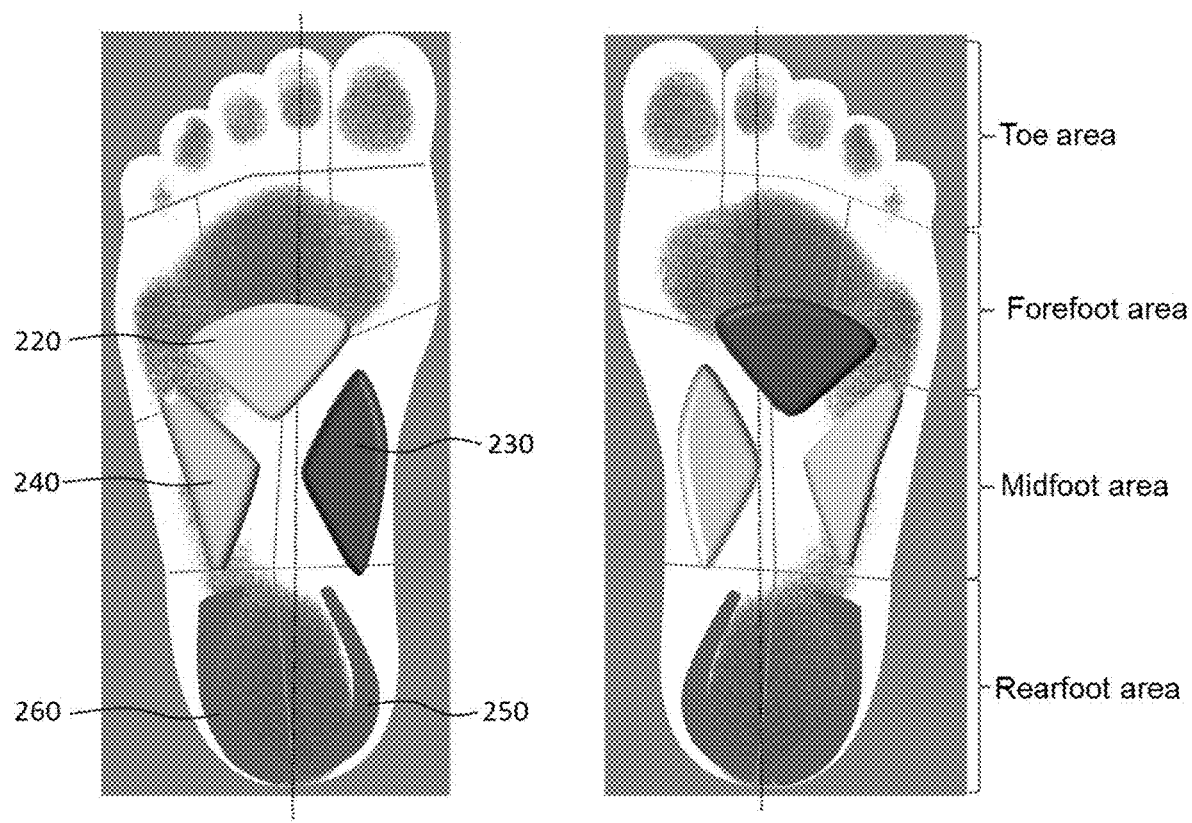
FIG. 6 is an attachment position diagram showing attachment positions of attachment pads in the personalized insole manufacturing apparatus according to an embodiment.
Figure 7:
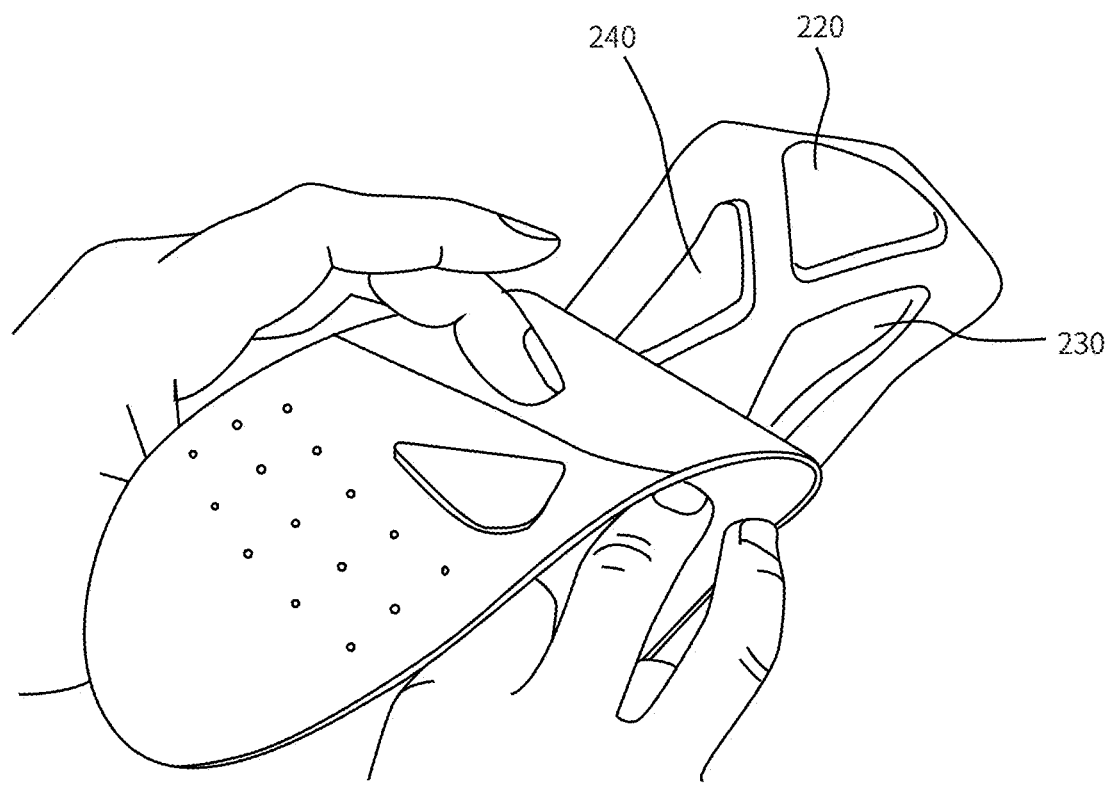
FIG. 7 is a diagram showing the attachment pad being attached to the insole according to an embodiment.

First, the foot pressure pattern pressure calculation unit 130 may divide the combined foot pressure pattern image 200 into a predetermined number of areas, as shown in FIGS. 5 and 6. For example, the foot pressure pattern pressure calculation unit 130 may divide the predetermined number of areas on the combined foot pressure pattern image into a toe area corresponding to the toe area, a forefoot area corresponding to an area from below the toe area to where the arch begins, a midfoot area corresponding to an area from where the arch ends to where the heel begins, and a rearfoot area corresponding to a heel area, and calculate the pressure level of each area based on the foot pressure pattern shown in the corresponding area. Furthermore, the foot pressure pattern pressure calculation unit 130 may divide the toe area of the combined foot pressure pattern image 200 into a first area 201 that is a predetermined area including the first toe, and a second area 202 that is a predetermined area including the four toes other than the first toe. In addition, the forefoot area may be divided into a third area 203 that is a predetermined inner area of the forefoot area, a fourth area 204 that is a predetermined middle area, and a fifth area 205 that is a predetermined outer area. In addition, the midfoot area may be divided with respect to the center into a sixth area 206 that is a predetermined inner area and a seventh area 207 that is a predetermined outer area. In addition, the rearfoot area may be divided with respect to the center into an eighth area 208 that is a predetermined inner area and a ninth area 209 that is a predetermined outer area.

For example, the foot pressure pattern pressure calculation unit 130 calculates the pressure level according to the difference in ink density of the foot pressure pattern appearing in each of the first to ninth areas, that is, calculates a high pressure level for areas with a high ink density and calculates a relatively low pressure level for areas with a low ink density. That is, the pressure level of each area may be calculated using a method of measuring the pressure level according to the difference in ink density. In addition, the foot pressure pattern pressure calculation unit 130 may use the difference in color that appears in each area to calculate the pressure level in the same manner as described above.

Furthermore, although there are differences in the size and shape of the foot shape between users, because the foot pressure pattern pressure calculation unit 130 divides each area based on the foot pressure pattern, it is possible to measure the pressure for each divided area while taking into account individual characteristics such as the differences in the size and shape of the foot shape of each user.

The insole attachment calculation unit 140 calculates an optimal attachment pad to be attached to the user's insole based on the pressure level for each area (toe, forefoot, midfoot, and rearfoot areas) or each of the first to ninth areas calculated from the foot pressure pattern pressure calculation unit 130.

For example, as shown in FIG. 6, the insole attachment calculation unit 140 may calculate a meta-dome pad 220 to support the sole of the user's foot at a position corresponding to a lower central area of the third to fifth areas of the combined image and an upper central area of the sixth and seventh areas by varying the shape, height, strength, or material. In addition, the insole attachment calculation unit 140 may calculate an arch pad 230 to support the sole of the user's foot at a position corresponding to the inside of the sixth area of the combined image by varying the shape, height, strength, or material. In addition, the insole attachment calculation unit 140 may calculate a forefoot lateral wedge pad 240 to support the sole of the user's foot at a position corresponding to the outside of the seventh area of the combined image by varying the shape, height, strength, or material. In addition, the insole attachment calculation unit 140 may calculate a medial heel wedge pad 250 to support the sole of the user's foot at a position corresponding to the inside of the eighth area of the combined image by varying the shape, height, strength, or material. In addition, the insole attachment calculation unit 140 may calculate a lateral heel wedge pad 260 to support the sole of the user's foot at a position corresponding to the outside of the ninth area of the combined image by varying the shape, height, strength, or material, or a combination thereof.

Figure 8:
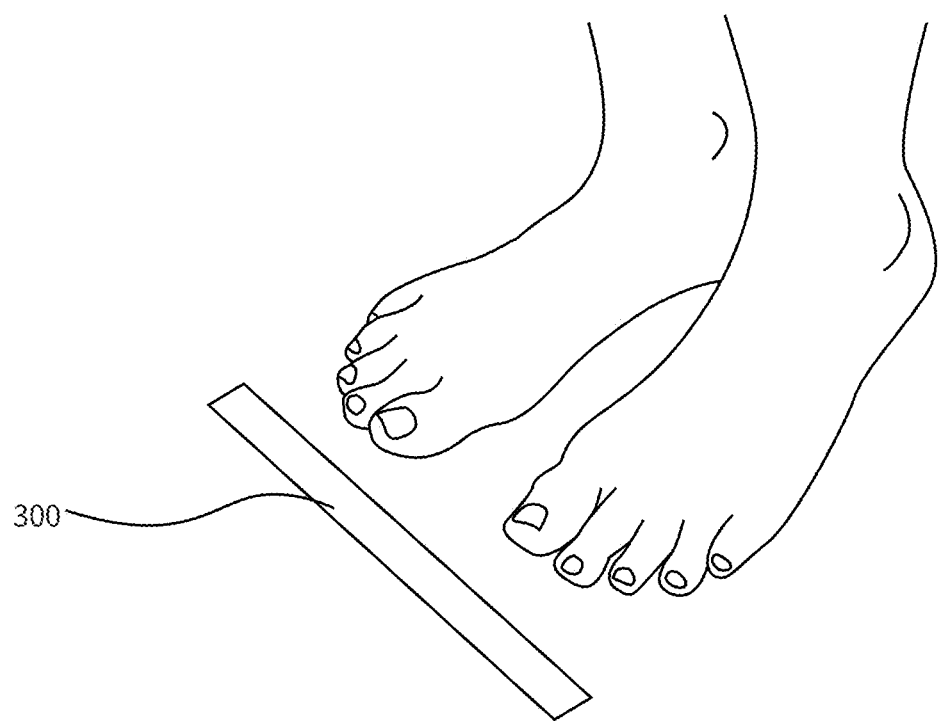
FIG. 8 is a diagram showing a reference line according to an embodiment.

The insole attachment output unit 150 may directly manufacture the attachment pad calculated by the insole attachment calculation unit 140 using a 3D printer 153, etc., transmit the data related to the attachment pad to a separate manufacturing apparatus (or molding apparatus) 154, display the calculated attachment pad or data related to the attachment pad through the display 151, or provide voice information on the calculated attachment pad through a speaker 152. In addition, when the display 151 or the speaker 152 is used as the insole attachment output unit 150, the overall usage or manufacturing process, etc. of the personalized insole manufacturing apparatus may be output and shown to the user. In addition, when informed of the data related to the attachment pad through the display 151 or the speaker 152, the user may select the type of pad informed from the insole attachment unit 170 that is provided with a plurality of attachment pads manufactured in advance. In addition, as shown in FIG. 8, it is possible to manufacture a personalized insole by attaching the selected attachment pad to a designated position on the upper or lower side of the insole, and wear the shoe after inserting the manufactured personalized insole into the bottom of the shoe.

Figure 4:
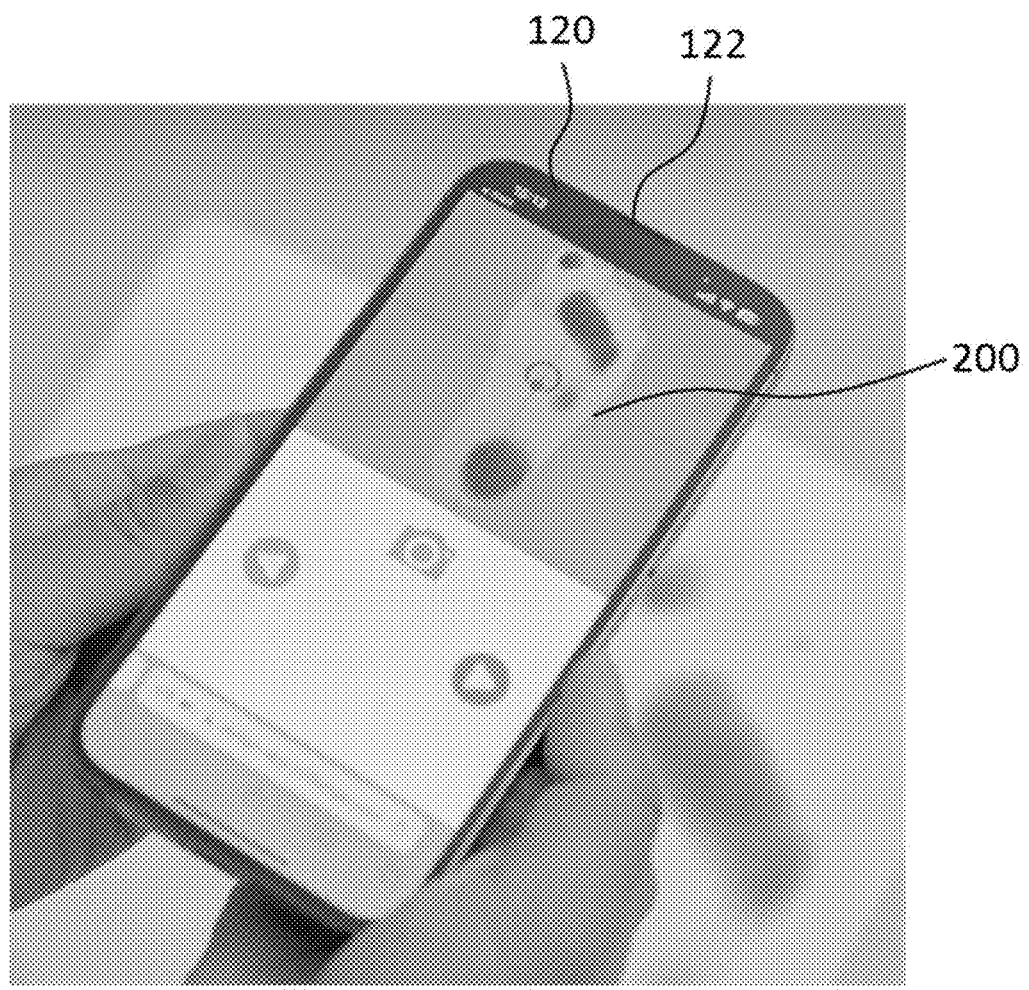
FIG. 4 is a diagram showing an image of a foot pressure pattern being acquired using a foot pressure pattern image acquisition unit.

Hereinafter, the method of calculating the attachment pad according to the foot pressure pattern in the insole attachment calculation unit 140 will be described in more detail. First, as shown in FIG. 4, with respect to the foot pressure pattern of the left, right, or both feet acquired and input from the foot pressure pattern image acquisition unit 120, the foot pressure pattern pressure calculation unit 130 compares a center line 211 of the midfoot with a virtual central reference line 212 that connects a front central point of the second toe and a rear central point of the rearfoot of the foot pressure pattern in a straight line as shown in FIG. 5, and evaluates it as normal when the center line 211 and the central reference line 212 coincide with each other within a predetermined error range, and calculates the meta-dome pad 220, the arch pad 230, and the forefoot lateral wedge pad 240 with the first level of strength, thickness, and elasticity and then outputs the calculated results through the insole attachment output unit 150. The center line 211 of the midfoot is the boundary line between the sixth area 206 and the seventh area 207, and it refers to an imaginary line connecting the bisector of the imaginary line connecting the widest part between the first metatarsophalangeal joint (1st MTPJ) and the fifth metatarsophalangeal joint (5th MTPJ) and the bisector of the imaginary line connecting the seventh area 207 and the narrowest part at the heel.

If the center line 211 does not coincide with the central reference line 212 and deviates therefrom by more than a predetermined error range, and if the boundary line 213 of the foot pressure pattern of the midfoot is in the sixth area 206, the foot is calculated to be in a state of falling inward, and is calculated as a flat foot or pronated foot, that is, a flat foot, and in the case of flat feet with the inner arch collapsed inward, in order to correct it to its normal state, the insole attachment calculation unit 140 calculates the meta-dome pad 220 and the forefoot lateral wedge pad 240 to have the first level of strength, thickness, and elasticity, and calculates the arch pad 240 to have the second level of strength, thickness, and elasticity, which is higher than the first level, and then inform the result to the user through the display or outputs the related data to the outside. For example, when the level of the attachment pad increases from the first level to the second level, the strength, thickness, and elasticity may all increase, or only one of the strength, thickness, and elasticity may increase. For example, Table 1 shows an embodiment of data calculated by the insole attachment calculation unit 140 and informed to the user through the display.

TABLE 1

| Insole Size | Color | Height (cm) | | | Shore A | | | Material | | |
| --- | --- | --- | --- | --- | --- | --- | --- | --- | --- | --- |
| | | Metadome | Arch pad | Lateral wedge | Meta-dome | Arch pad | Lateral wedge | Meta-dome | Arch pad | Lateral wedge |
| Large | Grey | 0.20 | 0.40 | 0.20 | 45 | 45 | 45 | Highly elastic polyurethane | Highly elastic polyurethane | Highly elastic polyurethane |
| | Yellow | 0.54 | 0.67 | 0.61 | 20 | 20 | 20 | Highly elastic polyurethane | Highly elastic polyurethane | Highly elastic polyurethane |
| | Red | 0.54 | 0.67 | 0.61 | 45 | 45 | 45 | Highly elastic polyurethane | Highly elastic polyurethane | Highly elastic polyurethane |
| Medium | Grey | 0.17 | 0.24 | 0.26 | 45 | 45 | 45 | Highly elastic polyurethane | Highly elastic polyurethane | Highly elastic polyurethane |
| | Yellow | 0.47 | 0.68 | 0.6 | 20 | 20 | 20 | Highly elastic polyurethane | Highly elastic polyurethane | Highly elastic polyurethane |
| | Red | 0.50 | 0.65 | 0.68 | 45 | 45 | 45 | Highly elastic polyurethane | Highly elastic polyurethane | Highly elastic polyurethane |
| Small | Grey | 0.17 | 0.14 | 0.25 | 45 | 45 | 45 | Highly elastic polyurethane | Highly elastic polyurethane | Highly elastic polyurethane |
| | Yellow | 0.54 | 0.58 | 0.60 | 20 | 20 | 20 | Highly elastic polyurethane | Highly elastic polyurethane | Highly elastic polyurethane |
| | Red | 0.57 | 0.70 | 0.70 | 45 | 45 | 45 | Highly elastic polyurethane | Highly elastic polyurethane | Highly elastic polyurethane |

[unit: mm, manufacturing deviation: ±0.02 mm]

In Table 1 above, Large, Medium, and Small indicate the size of the insole. In addition, Grey, Yellow, and Red indicate the level of the attachment pad. For example, Gray indicates the first level, Yellow indicates the second level, and Red indicates the third level. In addition, Height indicates the thickness of the attachment pad. In this way, the insole attachment calculation unit 140 may analyze the combined image to calculate various attachments to suit the user.

If the center line 211 does not coincide with the central reference line 212 and deviates therefrom by more than a predetermined error range, and if the boundary line of the midfoot pressure pattern is in the seventh area 230, the foot has a high arch or a rigid foot, and is calculated to be pes cavus, that is, high arch in which the arch does not flexibly and easily move up and down to support body weight during gait. A user with high arch has difficulty moving the body weight from the outside to the inside naturally, which causes a strong shock on the inside and outside of the midfoot, and in order to direct the body weight to the inside, the insole attachment calculation unit 140 calculates the meta-dome pad 220 and the arch pad 230 to have the first level of strength, thickness, and elasticity, and calculates the forefoot lateral wedge pad 240 to have the second level of strength, thickness, and elasticity, which is higher than the first level, and then inform this to the user through the display or outputs related data to the outside.

Next, by comparing the pressure levels of each of the two areas of the rearfoot calculated by the foot pressure pattern pressure calculation unit 130, the insole attachment calculation unit 140 additionally calculates the medial heel wedge pad 250 and outputs the result when the pressure level of the eighth area 208 is higher than the pressure level of the ninth area 209, and additionally calculates the lateral heel wedge pad 260 and then outputs the result when the pressure level of the eighth area 208 is lower than the pressure level of the ninth area 209. In addition, if the pressure levels of each of the eighth area 208 and the ninth area 209 are within a predetermined range, the separate heel wedge pads 250 and 260 are not calculated.

Next, when the comparison of the pressure levels of each of the three areas of the forefoot calculated by the foot pressure pattern pressure calculation unit 130 indicates the pressure levels in the order of the third area>the fourth area>the fifth area, or the pressure levels in the order of the fourth area>the third area>the fifth area, this means that the body weight is gradually shifted to the inside of the forefoot during gait. Accordingly, in order to support the lateral arch along with the support of the inner arch, the insole attachment calculation unit 140 recalculates the levels of the arch pad 230 and the meta-dome pad 220 so that the pads 230 and 220 have the strength, thickness, and elasticity increased by one level, respectively and output the result. In addition, when the pressure level of the fifth area is greater than those of the third and fourth areas, this points to the forefoot valgus in which the body weight is shifted outward once the foot touches the ground, in which case intoeing gait can develop. Accordingly, in order to prevent the body weight from shifting outward, the insole attachment calculation unit 140 recalculates the forefoot lateral wedge pad 220 to have the strength, thickness, and elasticity increased by one level and outputs the result through the display, or outputs the related data externally.

In addition, through the insole attachment output unit 150, for example, through a display or a speaker, a guidance screen may be output instructing the user to form a reference line 300 in a straight line on the ground, and a guidance message may be output instructing the user to position the ends of both left and right feet on the reference line, look straight ahead, and walk a predetermined number of steps in place with both feet. In addition, the personalized insole manufacturing apparatus may be provided with a user input unit 160 that can receive information from the user about where the left and right feet are positioned with respect to the reference line after the user stops walking in place according to the guidance message output through the display unit 150. The user input unit 160 may be a keyboard 161, mouse 162, or microphone 163 of an insole manufacturing apparatus or a mobile device. In addition, the foot pressure pattern image acquisition unit 120 may be used as the user input unit 160. The insole attachment calculation unit 140 may determine the relative positions of the left and right feet with respect to the reference line 300 received through the user input unit 160 and recalculate the previously calculated attachment pad.

In an embodiment, the user places both feet on the reference line, looks straight ahead, walks in place and then stops, and in this state, if the left foot is positioned ahead of the right foot relative to the reference line, or if the right foot is positioned behind the left foot, it means that the entire pelvis may be rotated clockwise. In this case, since the left foot is a mainly pronated foot in which the body weight is strongly shifted to the inside of the left foot, the insole attachment calculation unit 140 recalculates the strength, thickness and elasticity of the forefoot lateral wedge pad of the right foot so that the pad has the strength, thickness and elasticity increased by one level.

In an embodiment, the user places both feet on the reference line, looks straight ahead, walks in place and then stops, and in this state, if the right foot is positioned ahead of the left foot relative to the reference line, or if the left foot is positioned behind the right foot, it means that the entire pelvis is rotated counterclockwise. In this case, if the right foot is a pronated foot and the arch pad of the left foot is higher than the arch pad of the right foot, the movements of the pelvis and feet are different from each other. Accordingly, in order to prevent pelvic rotation first, the insole attachment calculation unit 140 recalculates the strength, thickness, and elasticity of the arch pad and meta-dome pad of the right foot to the strength, thickness, and elasticity increased by one level so as to direct the body weight to the outside of the right foot.

In addition, in an embodiment, the user places both feet on the reference line, looks straight ahead, walks in place and then stops, and in this state, if both feet are aligned on the same straight line, there is no pelvic rotation and a separate pad recalculation is not performed.

Preferably, through the insole attachment output unit 150, a guidance message may be output to check the presence or absence of symptoms of the user, such as whether squatting is possible, whether Achilles' tendinitis, metatarsalgia, and Morton's neuroma are present, whether ankle pain is present, and whether hallux valgus is present, and the user input unit 160 may receive information about the presence or absence of symptoms for each corresponding item from the user. In addition, the insole attachment calculation unit 140 may receive the information on the presence or absence of symptoms of the corresponding item from the user and recalculate the previously calculated attachment pad.

In an embodiment, when the user is unable to squat or has Achilles tendonitis, it is highly likely that the flexibility of the gastrocnemius muscle is low or soft tissue is adhered, making the muscle unable to stretch. In this case, the insole attachment calculation unit 140 recalculates both the medial heel wedge pad 250 and the lateral heel wedge pad 260 and outputs the result. When the user has metatarsalgia or Morton's neuroma, it is highly likely that transverse arch function is reduced and so there is inflammation and pain due to mechanical overload. In this case, in order to reduce the load and expand the space of the neural canal by opening the transverse arches, the insole attachment calculation unit 140 recalculates the attachment pad by raising the strength, thickness, and elasticity values of the meta-dome pad 220 to the third level.

In addition, when the user has ankle pain, in most cases, excessive fatigue has accumulated in the peroneus longus or peroneus brevis muscle. Accordingly, in order to prevent the foot from leaning outward as much as possible, the insole attachment calculation unit 140 recalculates the forefoot lateral wedge pad that can control the valgus force. In addition, when the user has hallux valgus, in most cases, it is accompanied with bunions that cause inflammation in the first metatarsophalangeal joint. Accordingly, the insole attachment calculation unit 140 recalculates the meta-dome pad so as to raise the transverse arch as much as possible to lift the bunions and reduce physical pressure and frequent contact.

The insole attachment unit 170 may be a pad container provided with the meta-dome pad 220, the arch pad 230, the forefoot lateral wedge pad 240, the medial heel wedge pad 250, and the lateral heel wedge pad 260 having the first to third levels of strength, thickness, and elasticity, which may be manufactured in advance for user convenience and reduction of manufacturing costs.

Preferably, the meta-dome pad 220, the arch pad 230, and the forefoot lateral wedge pad 240 may have strengths or thicknesses ranging from first to third levels, and the strengths and thicknesses may be combined with each other. Therefore, according to these combinations, the meta-dome pad 220, the arch pad 230, and the forefoot lateral wedge pad 240 may be provided in three or more types, and the medial heel wedge pad 250 and lateral heel wedge pad 260 may be provided in one type each.

Each pad provided in the insole attachment portion 170 may be provided in a combination of not only the strength, thickness, and elasticity, but also different materials, and the shape of each pad may be formed differently, and the differences in the shape, strength, thickness, and elasticity of the pad may be distinguished by color. That is, the meta-dome pad, the arch pad, and the forefoot lateral wedge pad may have different shapes to correspond to their respective attachment positions, and the strength, thickness and elasticity of the meta-dome pad, the arch pad and the forefoot lateral wedge pad may be distinguished with, for example, different colors for each level, such as gray for the first level pad, yellow for the second level pad, and red for the third level pad, thus allowing the user to easily distinguish the attachments and attach the attachments to the insole. In an embodiment, from the first level to the third level, the strength of the pad may increase, the height may also increase, and the elasticity may also increase from low to high.

As described above, the optimum pads for the user calculated at the insole attachment calculation unit 140 may be displayed through the insole attachment output unit 150 such as a display, for example. The user may get the same type of pad as the pad identified through the display from the insole attachment unit 170 and attach the same to the insole.

As described above, the personalized insole manufacturing apparatus enables a user to more conveniently manufacture a personalized insole by simplifying the positions and types of attachments required to be attached to the insole through the measured foot pressure pattern, and also enables the user to manufacture a more accurate and personalized insole in response to the individual user's physical characteristics or medical conditions, by calculating the positions and types of the insole attachments after considering not only the pressure applied by the body weight distribution and movement that appears during the user's gait, but also the degree of distortion of the user's pelvis and the existing medical conditions that each user may have.

Although several embodiments have been described above as examples, it is obvious to those skilled in the art that the present disclosure may be embodied in various other forms without departing from the spirit and scope thereof.

Accordingly, the embodiments described herein are to be regarded as illustrative and not restrictive, and all embodiments within the appended claims and their equivalents are intended to be included within the scope of the present disclosure.

The invention claimed is:

1. A personalized insole manufacturing apparatus comprising:
    a foot pressure pattern measuring unit configured to measure user's foot pressure pattern, wherein the foot pressure pattern measuring unit has adhesive properties so as to be attached to a sole of the user's foot and is configured to print differently between an area on which a high pressure is applied by the user's body weight and an area on which a low pressure is applied;
    a foot pressure pattern image acquisition unit configured to capture an image of the foot pressure pattern printed on the foot pressure pattern measuring unit and combine the captured image with a foot shape image, wherein the foot pressure pattern image acquisition unit includes a camera and an image processing application;
    a user input unit including a keyboard, mouse, or microphone, wherein the user input unit is configured to receive information from a user;
    a foot pressure pattern pressure calculation unit including a processor configured to receive, from the foot pressure pattern image acquisition unit, a combined image of the foot pressure pattern and the foot shape image, divide the received combined image into a predetermined number of areas according to a predetermined criteria, analyze the foot pressure pattern printed in each area, and calculate a pressure level for each area;
    an insole attachment calculation unit including a processor configured to calculate data on shape, height, strength, elasticity, or material of an attachment pad corresponding to the foot pressure pattern based on the pressure level for each area received from the foot pressure pattern pressure calculation unit; and
    an insole attachment output unit including a display configured to visually show the attachment pad or data calculated by the insole attachment calculation unit, or a speaker configured to provide voice guidance,
    wherein the foot pressure pattern measuring unit includes a thin plate-shaped pad that displays the area on which the large pressure is applied by the body weight and the area on which the small pressure is applied with different ink densities or different colors, and
    the processors included in the foot pressure pattern pressure calculation unit and the insole attachment calculation unit are hardware processors or software processors, and the processors included in the foot pressure pattern pressure calculation unit and the insole attachment calculation unit are separate processors or the same processor.

2. The personalized insole manufacturing apparatus according to claim 1, further comprising an insole attachment unit provided with a plurality of attachment pads having different combinations of shapes, heights, strengths, and materials, wherein the insole attachment calculation unit displays the calculated attachment pads through a display.

3. The personalized insole manufacturing apparatus according to claim 1, wherein the foot pressure pattern pressure calculation unit divides the predetermined number of areas on the combined image into:
    a toe area corresponding to a toe portion;
    a forefoot area corresponding to an area from below the toe area to where arch begins;
    a midfoot area corresponding to an area from where the arch ends to where heel begins; and
    a rearfoot area corresponding to a heel area.

4. The personalized insole manufacturing apparatus according to claim 3, wherein the foot pressure pattern pressure calculation unit further divides the predetermined number of areas on the combined foot pressure pattern image into:
for the toe area, a first area as an area including a first toe, and a second area as an area including four other toes except the first toe;
for the forefoot area, a third area as an inner area of the forefoot area, a fourth area as a middle area, and a fifth area as an outer area,
for the midfoot area, a sixth area as an inner area with respect to a center and a seventh area as an outer area with respect to the center, and
for the rearfoot area, an eighth area as an inner area with respect to the center and a ninth area as an outer area with respect to the center, and
calculates a pressure level of each area based on the foot pressure pattern shown in each area.

5. The personalized insole manufacturing apparatus according to claim 4, wherein the attachment pad calculated by the insole attachment calculation unit includes:
a meta-dome pad configured to support a sole of the user's foot at a position corresponding to a lower central area of the third to fifth areas and an upper central area of the sixth and seventh areas of the combined image;
an arch pad configured to support the sole of a user's foot at a position corresponding to an inside of the sixth area of the combined image;
a forefoot lateral wedge pad configured to support the sole of the user's foot at a position corresponding to an outside of the seventh area of the combined image;
a medial heel wedge pad configured to support the sole of the user's foot at a position corresponding to an inside of the eighth area of the combined image; and
a lateral heel wedge pad configured to support the sole of the user's foot at a position corresponding to an outside of the ninth area of the combined image, and
the insole attachment calculation unit calculates each pad by varying a combination of shape, height, strength, and material.

6. The personalized insole manufacturing apparatus according to claim 1, wherein the insole attachment output unit is a 3D printer or molding apparatus configured to receive the data about the attachment pad calculated by the insole attachment calculation unit and manufacture the attachment pad.

7. The personalized insole manufacturing apparatus according to claim 5, wherein the insole attachment calculation unit is configured to:
compare a virtual boundary line of the sixth and seventh areas with a virtual central reference line connecting a front central point of the second toe and a rear central point of a rearfoot of the foot pressure pattern in a straight line, and when the center line and the central reference line coincide with each other within a predetermined error range, calculate the meta-dome pad, the arch pad, and the forefoot lateral wedge pad to have a first level thickness;
when the center line does not coincide with the central reference line within the predetermined error range and the boundary line of the foot pressure pattern of the midfoot is in the sixth area, calculate the meta-dome pad and the forefoot lateral wedge pad to have the first level thickness, and calculate the arch pad to have a second level thickness which is higher than the first level; and
when the center line does not coincide with the central reference line within the predetermined error range and the boundary line of the foot pressure pattern of the midfoot is in the seventh area, calculate the meta-dome pad and arch pad to have the first level thickness, and calculate the forefoot lateral wedge pad to have the second level thickness which is higher than the first level.

8. The personalized insole manufacturing apparatus according to claim 7, wherein the insole attachment calculation unit is configured to:
when the pressure level of the eighth area is higher than the pressure level of the ninth area, calculate the medial heel wedge pad to have a predetermined height; and
when the pressure level of the eighth area is lower than the pressure level of the ninth area, calculate the lateral heel wedge pad to have a predetermined height.

9. The personalized insole manufacturing apparatus according to claim 8, wherein the insole attachment calculation unit is configured to:
when the pressure level of the third area and the pressure level of the fourth area are greater than the pressure level of the fifth area, recalculate each thickness of the arch pad and the meta-dome pad by increasing the thickness by one level; and
when the pressure level of the fifth area is greater than the pressure levels of the third and fourth areas, recalculate the thickness of the forefoot lateral wedge pad by increasing the thickness by one level.

10. The personalized insole manufacturing apparatus according to claim 5, wherein the insole attachment calculation unit is configured to:
after the user looks straight ahead, walks in place and then stops, if information is received from the input unit that a user's left foot is positioned ahead of the right foot, recalculate the thickness of the forefoot lateral wedge pad of the right foot by increasing the thickness by one level; and
when information is received from the input unit that the right foot is positioned ahead of the left foot relative to the reference line, recalculate the thicknesses of the arch pad and the meta-dome pad of the right foot by increasing each thickness by one level.

11. The personalized insole manufacturing apparatus according to claim 5, further comprising a container provided with the meta-dome pad, the arch pad, the forefoot lateral wedge pad, the medial heel wedge pad, and the lateral heel wedge pad manufactured in advance, wherein the pads have first to third levels of thicknesses.

12. A method for manufacturing a personalized insole, comprising:
attaching a foot pressure pattern measurement pad to a sole of a user's foot to measure a user's foot pressure pattern when a user walks a predetermined distance;
capturing, by a camera, an image of the foot pressure pattern printed on the foot pressure pattern measurement pad, and generating, by an image processing application, a combined image by combining the foot pressure pattern with a foot shape image;
by a foot pressure pattern pressure calculation processor, dividing the combined image into a predetermined number of areas according to a predetermined criteria, analyzing the foot pressure pattern printed in each area, and calculating a pressure level for each area;
calculating, by an insole attachment calculation processor, data on shape, height, strength, elasticity, or material of an attachment pad corresponding to the foot pressure pattern based on the pressure level of each area received from the foot pressure pattern pressure calculation processor; and outputting, through one or more of a display, a speaker, a 3D printer, or a molding apparatus, the attachment pad or the data calculated by the insole attachment calculation processor, wherein the foot pressure pattern displays an area on which a large pressure is applied by body weight and an area on which a small pressure is applied with different ink densities or different colors, and the predetermined number of areas on the combined foot pressure pattern image divided by the foot pressure pattern pressure calculation processor are divided into:
a toe area corresponding to a toe portion;
a forefoot area corresponding to an area from below the toe area to where arch begins;
a midfoot area corresponding to an area from where the arch ends to where heel begins; and
a rearfoot area corresponding to a heel area.

13. The method according to claim 12, comprising further dividing the predetermined number of areas on the combined foot pressure pattern image into:
for the toe area, a first area as an area including a first toe, and a second area as an area including four other toes except the first toe;
for the forefoot area, a third area as an inner area of the forefoot area, a fourth area as a middle area, and a fifth area as an outer area;
for the midfoot area; a sixth area as an inner area with respect to a center and a seventh area as an outer area with respect to the center; and
for the rearfoot area, an eighth area as an inner area with respect to the center and a ninth area as an outer area with respect to the center, and
calculating a pressure level of each area based on the foot pressure pattern shown in each area.

14. The method according to claim 13, wherein the attachment pad calculated by the insole attachment calculation processor includes:
a meta-dome pad configured to support a sole of the user's foot at a position corresponding to a lower central area of the third to fifth areas and an upper central area of the sixth and seventh areas of the combined image;
an arch pad configured to support the sole of a user's foot at a position corresponding to an inside of the sixth area of the combined image;
a forefoot lateral wedge pad configured to support the sole of the user's foot at a position corresponding to an outside of the seventh area of the combined image;
a medial heel wedge pad configured to support the sole of the user's foot at a position corresponding to an inside of the eighth area of the combined image; and
a lateral heel wedge pad configured to support the sole of the user's foot at a position corresponding to an outside of the ninth area of the combined image, and
the insole attachment calculation processor calculates each pad by varying a combination of shape, height, strength, and material.

15. The method according to claim 14, wherein the calculating, by the insole attachment calculation processor, the data on the shape, height, strength, elasticity, or material of the attachment pad includes:

comparing a virtual boundary line of the sixth and seventh areas with a virtual central reference line connecting a front central point of the second toe and a rear central point of a rearfoot of the foot pressure pattern in a straight line, and when the center line and the central reference line coincide with each other within a predetermined error range, calculating the meta-dome pad, the arch pad, and the forefoot lateral wedge pad to have a first level thickness;

when the center line does not coincide with the central reference line within the predetermined error range and the boundary line of the foot pressure pattern of the midfoot is in the sixth area, calculating the meta-dome pad and the forefoot lateral wedge pad to have the first level thickness, and calculating the arch pad to have a second level thickness which is higher than the first level; and when the center line does not coincide with the central reference line within the predetermined error range and the boundary line of the foot pressure pattern of the midfoot is in the seventh area, calculating the meta-dome pad and arch pad to have the first level thickness, and calculating the forefoot lateral wedge pad to have the second level thickness which is higher than the first level.

16. The method according to claim 15, wherein the calculating, by the insole attachment calculation processor, the data on the shape, height, strength, elasticity, or material of the attachment pad includes:
when the pressure level of the eighth area is higher than the pressure level of the ninth area, calculating the medial heel wedge pad; and
when the pressure level of the eighth area is lower than the pressure level of the ninth area, calculating the lateral heel wedge pad.

17. The method according to claim 16, wherein the calculating, by the insole attachment calculation processor, the data on the shape, height, strength, elasticity, or material of the attachment pad includes:
when the pressure level of the third area and the pressure level of the fourth area are greater than the pressure level of the fifth area, respectively, recalculating each thickness of the arch pad and the meta-dome pad by increasing the thickness by one level; and
when the pressure level of the fifth area is greater than the pressure levels of the third and fourth areas, respectively, recalculating the thickness of the forefoot lateral wedge pad by increasing the thickness by one level.

18. The method according to claim 14, wherein the calculating, by the insole attachment calculation processor, the data on the shape, height, strength, elasticity, or material of the attachment pad includes:
after the user looks straight ahead, walks in place and then stops, if information is received from the input unit that a user's left foot is positioned ahead of the right foot, recalculating the thickness of the forefoot lateral wedge pad of the right foot by increasing the thickness by one level; and
when information is received from the input unit that the right foot is positioned ahead of the left foot relative to the reference line, recalculating the thicknesses of the arch pad and the meta-dome pad of the right foot by increasing each thickness by one level.

* * * * *